(12) United States Patent
Lee et al.

(10) Patent No.: US 9,158,201 B2
(45) Date of Patent: Oct. 13, 2015

(54) MONOMER FOR HARDMASK COMPOSITION AND HARDMASK COMPOSITION INCLUDING THE MONOMER AND METHOD OF FORMING PATTERNS USING THE HARDMASK COMPOSITION

(71) Applicants: Bum-Jin Lee, Uiwang-si (KR); Yun-Jun Kim, Uiwang-si (KR); Youn-Jin Cho, Uiwang-si (KR)

(72) Inventors: Bum-Jin Lee, Uiwang-si (KR); Yun-Jun Kim, Uiwang-si (KR); Youn-Jin Cho, Uiwang-si (KR)

(73) Assignee: CHEIL INDUSTRIES, INC., Gumi-si, Kyeongsangbuk-do (KR)

( * ) Notice: Subject to any disclaimer, the term of this patent is extended or adjusted under 35 U.S.C. 154(b) by 16 days.

(21) Appl. No.: 14/079,990

(22) Filed: Nov. 14, 2013

(65) Prior Publication Data

US 2014/0186775 A1 Jul. 3, 2014

(30) Foreign Application Priority Data

Dec. 28, 2012 (KR) ........................ 10-2012-0157576

(51) Int. Cl.
G03F 7/11 (2006.01)
C07C 33/36 (2006.01)
G03F 7/26 (2006.01)
G03F 7/09 (2006.01)

(52) U.S. Cl.
CPC ........ G03F 7/26 (2013.01); G03F 7/094 (2013.01); C07C 33/36 (2013.01)

(58) Field of Classification Search
CPC ............ G03F 7/09; G03F 7/095; G03F 7/11; G03F 7/20; C07C 139/04; C07C 39/06; C07C 39/10; C07C 39/16; C07C 39/17; C07C 31/02; C07C 31/25; C07C 33/14; C07C 33/16; C07C 33/18; C07C 33/24; C07C 33/36

See application file for complete search history.

(56) References Cited

U.S. PATENT DOCUMENTS

| 2010/0119980 A1 | 5/2010 | Rahman et al. |
| 2011/0155944 A1 | 6/2011 | Cho et al. |
| 2013/0144005 A1* | 6/2013 | Wu et al. ..................... 524/588 |

FOREIGN PATENT DOCUMENTS

| CN | 101078787 A | | 11/2007 |
| CN | 102562281 A | | 7/2012 |
| EP | 2251386 | * | 11/2010 |
| JP | 06-102680 | * | 4/1994 |
| KR | 10-2001-0043652 A | | 5/2001 |
| KR | 10-2009-0068444 A | | 6/2009 |
| KR | 10-2010-0080147 A | | 7/2010 |
| KR | 10-2011-0079201 A | | 7/2011 |
| KR | 10-2011-0084901 A | | 7/2011 |
| KR | 10-2012-0068379 A | | 6/2012 |
| TW | 200906890 A | | 2/2009 |
| WO | WO 2010/055373 A1 | | 5/2010 |

OTHER PUBLICATIONS

Machine translation of the abstract of JP 06-102680, published on Apr. 15, 1994.*
Machine translation of JP 06-102680 published on Apr. 15, 1994.*
Machine translation of CN 101078787, published on Nov. 28, 2007.*
Machine translation of CN 102562281, published on Jul. 11, 2012.*
Chinese Search Report for 201310535509.1 dated Mar. 31, 2015; Lee, et al.
Taiwanese Search Report for 102140509 dated Jun. 29, 2015; Lee, et al.

* cited by examiner

Primary Examiner — Anca Eoff
(74) Attorney, Agent, or Firm — Lee & Morse, P.C.

(57) ABSTRACT

A monomer for a hardmask composition is represented by the following Chemical Formula 1,

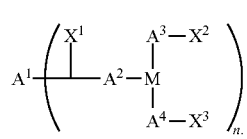

[Chemical Formula 1]

15 Claims, No Drawings

MONOMER FOR HARDMASK COMPOSITION AND HARDMASK COMPOSITION INCLUDING THE MONOMER AND METHOD OF FORMING PATTERNS USING THE HARDMASK COMPOSITION

CROSS-REFERENCE TO RELATED APPLICATION

Korean Patent Application No. 10-2012-0157576, filed on Dec. 28, 2012, in the Korean Intellectual Property Office, and entitled: "Monomer For Hardmask Composition and Hardmask Composition Including The Monomer and Method of Forming Patterns Using The Hardmask Composition," is incorporated by reference herein in its entirety.

BACKGROUND

1. Field

A monomer, a hardmask composition including the monomer and a method of forming patterns using the hardmask composition are disclosed.

2. Description of the Related Art

The semiconductor industry has developed an ultra-fine technique having a pattern of several to several tens nanometer size. Such an ultrafine technique uses lithographic techniques.

SUMMARY

Embodiments are directed to a monomer for a hardmask composition, the monomer being represented by the following Chemical Formula 1:

[Chemical Formula 1]

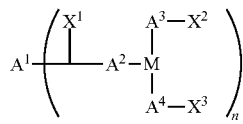

In the above Chemical Formula 1, $A^1$ may be a substituted or unsubstituted aliphatic cyclic group or a substituted or unsubstituted aromatic cyclic group, $A^2$ to $A^4$ may each be a phenylene group, $X^1$ to $X^3$ may each independently be a hydroxy group, a thionyl group, a thiol group, a cyano group, a substituted or unsubstituted amino group, a substituted or unsubstituted C1 to C30 alkyl group, a substituted or unsubstituted C1 to C20 alkylamine group, or a substituted or unsubstituted C1 to C30 alkoxy group, M may be $CR^a$, $SiR^b$, N, P, $PR^cR^d$, or $PR^e$, wherein $R^a$, $R^b$, $R^c$, and $R^d$ may each independently be hydrogen, a substituted or unsubstituted C1 to C10 alkyl group, a halogen atom, a halogen-containing group, or a combination thereof, and $R^e$ may be oxygen (O) or sulfur (S), and n may be an integer ranging from 1 to 4.

$A^1$ may be a substituted or unsubstituted cyclic group selected from the following Group 1:

[Group 1]

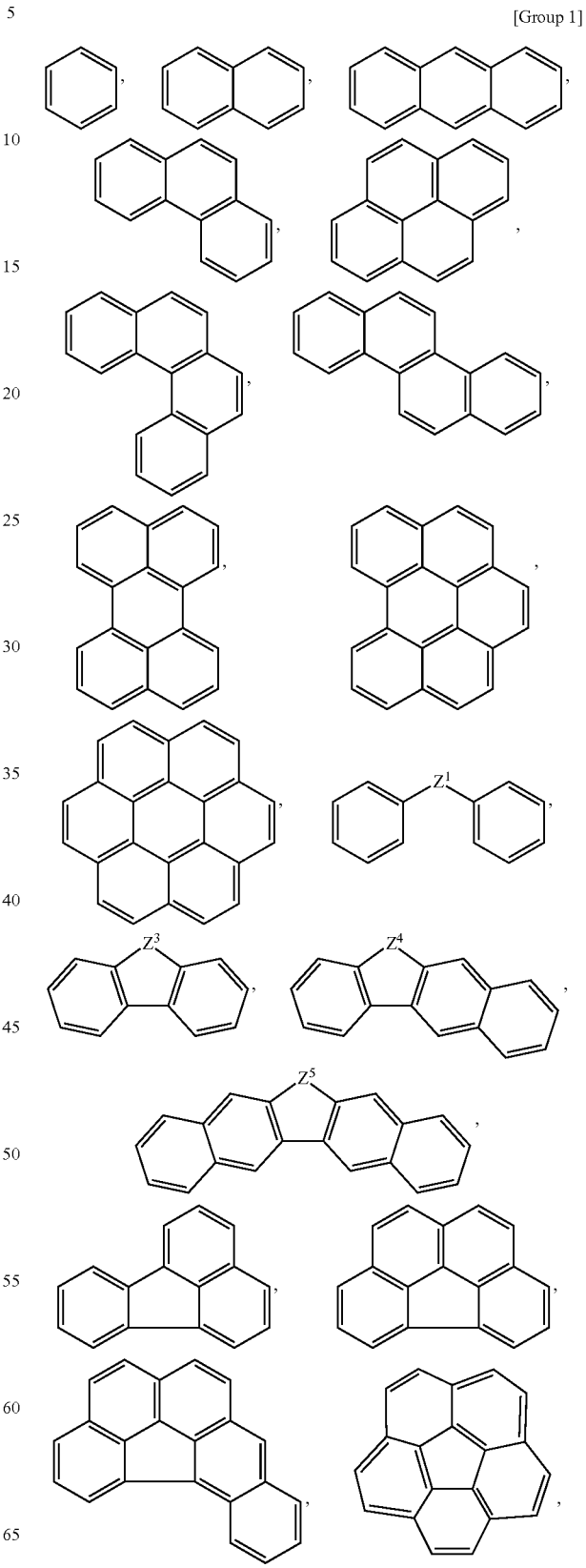

-continued

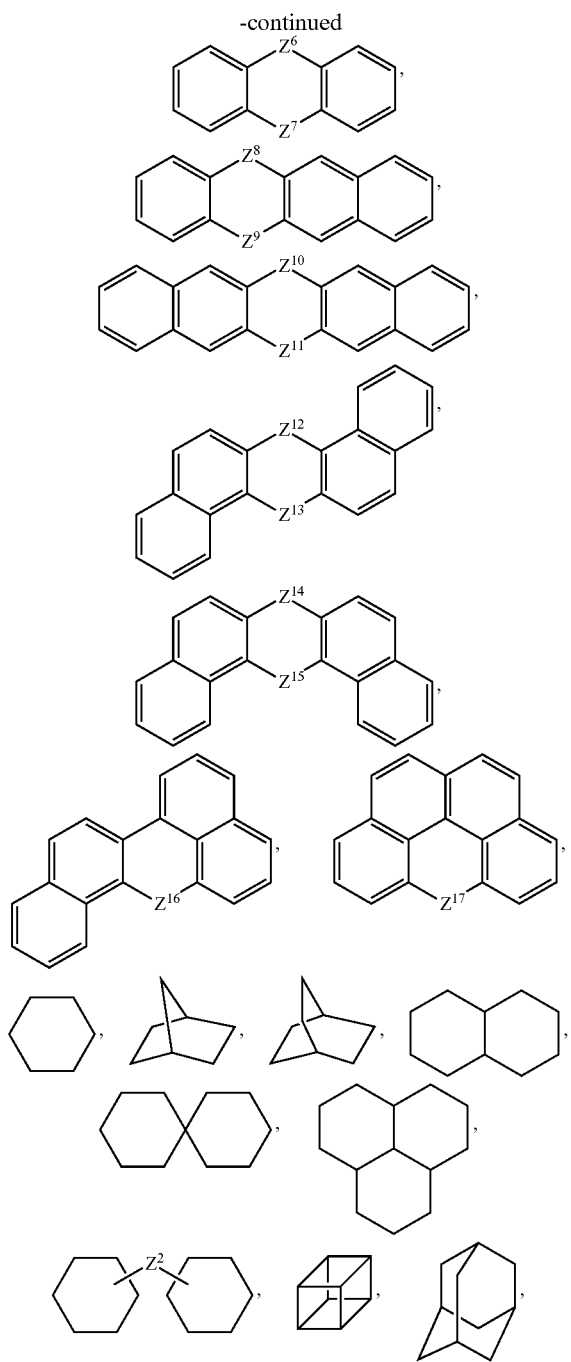

In Group 1, $Z^1$ and $Z^2$ may each independently be a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, C=O, $NR^f$, oxygen (O), sulfur (S), or a combination thereof, wherein $R^f$ may be hydrogen, a substituted or unsubstituted C1 to C10 alkyl group, a halogen atom, or a combination thereof, and $Z^3$ to $Z^{17}$ may independently be C=O, $NR^g$, oxygen (O), sulfur (S), $CR^hR^i$, or a combination thereof, wherein $R^g$ to $R^i$ may each independently be hydrogen, a substituted or unsubstituted C1 to C10 alkyl group, a halogen atom, a halogen-containing group, or a combination thereof.

$X^1$ may be a hydroxy group.

$A^1$ may be a substituted or unsubstituted divalent pyrene, benzoperylene, or coronene group, $A^2$ to $A^4$ may each be a phenylene group, $X^1$ may be a hydroxy group, and $X^2$ to $X^3$ may each independently be a hydroxy group, a thionyl group, a thiol group, a cyano group, a substituted or unsubstituted amino group, a substituted or unsubstituted C1 to C30 alkyl group, a substituted or unsubstituted C1 to C20 alkylamine group, or a substituted or unsubstituted C1 to C30 alkoxy group, M may be $CR^a$, wherein $R^a$ may be hydrogen, a substituted or unsubstituted C1 to C10 alkyl group, a halogen atom, a halogen-containing group, or a combination thereof, and n may be 2.

The monomer may be represented by the following Chemical Formula 2, Chemical Formula 3, or Chemical Formula 4:

[Chemical Formula 2]

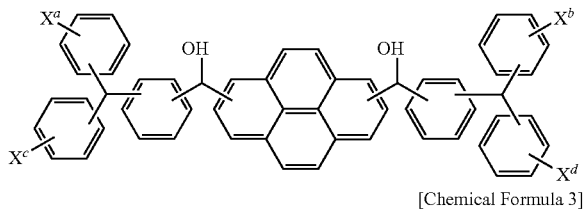

[Chemical Formula 3]

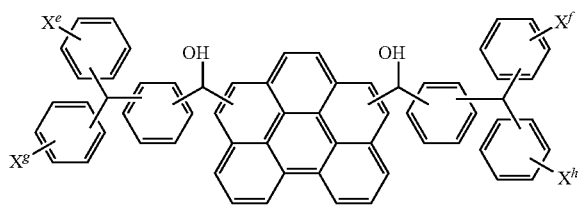

[Chemical Formula 4]

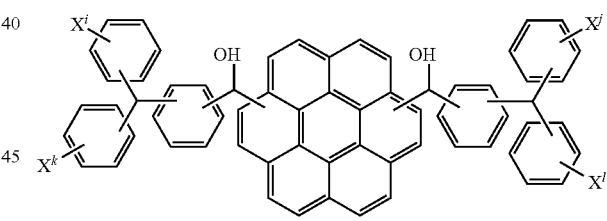

In the above Chemical Formulae 2 to 4, $X^a, X^b, X^c, X^d, X^e, X^f, X^g, X^h, X^i, X^j, X^k$, and $X^l$ may each independently be a hydroxy group, a thionyl group, a thiol group, a cyano group, a substituted or unsubstituted amino group, a substituted or unsubstituted C1 to C30 alkyl group, a substituted or unsubstituted C1 to C20 alkylamine group, or a substituted or unsubstituted C1 to C30 alkoxy group.

The monomer may have a molecular weight of about 300 to about 3,000.

Embodiments are also directed to a hardmask composition, including a monomer represented Chemical Formula 1 and a solvent.

The monomer may be included in an amount of about 1 to about 50 wt % based on the total amount of the hardmask composition.

Embodiments are also directed to a method of forming patterns, including providing a material layer on a substrate, applying the hardmask composition according to an embodiment on the material layer;

heat-treating the hardmask composition to form a hardmask layer;

forming a silicon-containing thin layer on the hardmask layer;

forming a photoresist layer on the silicon-containing thin layer;

exposing and developing the photoresist layer to form a photoresist pattern;

selectively removing the silicon-containing thin layer and the hardmask layer using the photoresist pattern to expose a part of the material layer; and etching an exposed part of the material layer.

The hardmask composition may be applied using a spin-on coating method.

DETAILED DESCRIPTION

Example embodiments will now be described more fully hereinafter. These embodiments are provided so that this disclosure will be thorough and complete, and will fully convey example implementations to those skilled in the art.

In this specification, when a definition is not otherwise provided, 'substituted' refer to one substituted with a substituent selected from a halogen atom (F, Cl, Br, or I), a hydroxy group, an alkoxy group, a nitro group, a cyano group, an amino group, an azido group, an amidino group, a hydrazino group, a hydrazono group, carbonyl group, a carbamyl group, a thiol group, an ester group, a carboxyl group or a salt thereof, a sulfonic acid group or a salt thereof, a phosphoric acid or a salt thereof, a C1 to C20 alkyl group, a C2 to C20 alkenyl group, a C2 to C20 alkynyl group, a C6 to C30 aryl group, a C7 to C30 arylalkyl group, a C1 to C4 alkoxy group, a C1 to C20 heteroalkyl group, a C3 to C20 heteroarylalkyl group, a C3 to C30 cycloalkyl group, a C3 to C15 cycloalkenyl group, a C6 to C15 cycloalkynyl group, a C2 to C30 heterocycloalkyl group, and a combination thereof, instead of hydrogen atom of a compound.

In this specification, when a definition is not otherwise provided, 'hetero' refers to one including 1 to 3 heteroatoms selected from N, O, S, and P.

Hereinafter, a monomer for a hardmask composition according to an example embodiment is described.

A monomer for a hardmask composition according to an example embodiment is represented by the following Chemical Formula 1.

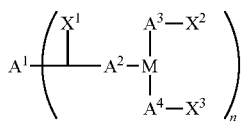

[Chemical Formula 1]

According to the present example embodiment, in the above Chemical Formula 1, $A^1$ is a substituted or unsubstituted aliphatic cyclic group or a substituted or unsubstituted aromatic cyclic group, $A^2$ to $A^4$ are each a phenylene group, $X^1$ to $X^3$ are each independently a hydroxy group, a thionyl group, a thiol group, a cyano group, a substituted or unsubstituted amino group, a substituted or unsubstituted C1 to C30 alkyl group, a substituted or unsubstituted C1 to C20 alkylamine group, or a substituted or unsubstituted C1 to C30 alkoxy group, M is $CR^a$, $SiR^b$, N, P, $PR^cR^d$, or $PR^e$, and n is an integer ranging from 1 to 4.

In the M, $R^a$, $R^b$, $R^c$, and $R^d$ are each independently hydrogen, a substituted or unsubstituted C1 to C10 alkyl group, a halogen atom, a halogen-containing group, or a combination thereof, and $R^e$ is oxygen (O) or sulfur (S).

According to the present example embodiment, the monomer is a compound including an aliphatic cyclic group or aromatic cyclic group having one or more than two rings as a core and a triphenyl structure as a substituent and has a rigid characteristic, and thus, properties of the monomer may be easily adjusted depending on the substituent.

The monomer may have improved solubility due to a plurality of functional groups ($X^1$ to $X^3$) in each substituent, and thus may be useful for a spin-on coating method, may have improved gap-fill characteristics to fill a gap, and may have planarization characteristics when the monomer is formed using a spin-on coating method on a lower layer having a predetermined pattern.

Amplified cross-linking reactions may be performed due to a condensation reaction with the plurality of functional groups, and thereby excellent cross-linking characteristics may be realized. Therefore, even when the monomer is heat-treated at a relatively low temperature, the monomer may be cross-linked to form a high molecular weight polymer in a short time. Thus, characteristics desired in a hardmask layer, such as excellent mechanical characteristics, heat resistance characteristics, chemical resistance, and etch resistance, may be provided.

In an example embodiment, $A^1$ may be a substituted or unsubstituted cyclic group selected from the following Group 1.

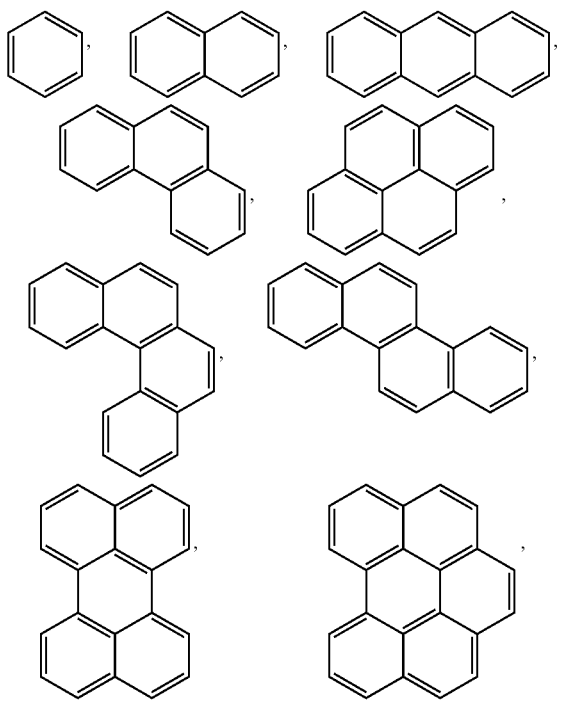

[Group 1]

-continued

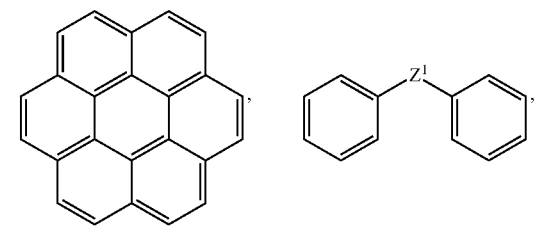
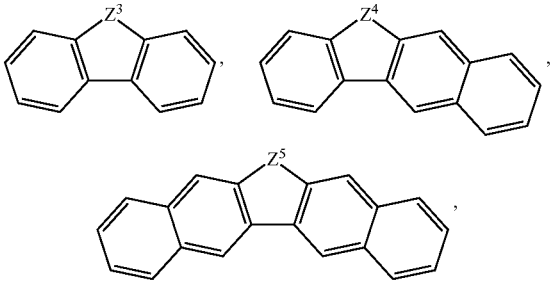
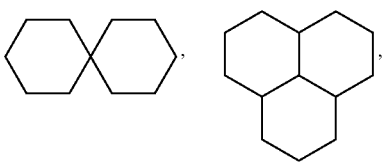
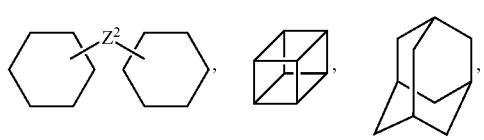

-continued

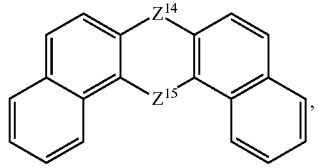
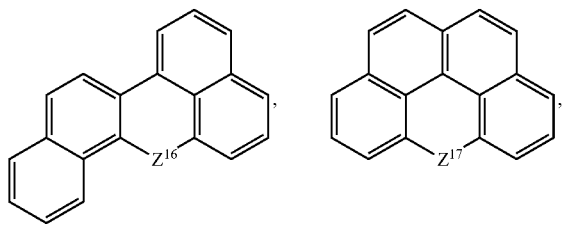
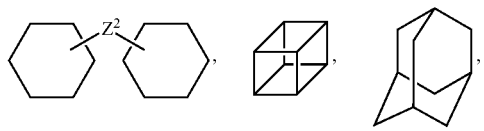

According to the present example embodiment, in Group 1, $Z^1$ and $Z^2$ are each independently a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, C=O, $NR^f$, oxygen (O), sulfur (S), or a combination thereof, wherein $R^f$ is hydrogen, a substituted or unsubstituted C1 to C10 alkyl group, a halogen atom, or a combination thereof, and $Z^3$ to $Z^{17}$ are independently C=O, $NR^g$, oxygen (O), sulfur (S), $CR^hR^i$, or a combination thereof, wherein $R^g$ to $R^i$ are each independently hydrogen, a substituted or unsubstituted C1 to C10 alkyl group, a halogen atom, a halogen-containing group, or a combination thereof.

In Group 1, a linking position of each ring is not particularly limited, and each ring may be substituted or unsubstituted. When the Group 1 ring is a substituted ring, it may be substituted with, for example, a C1 to C20 alkyl group, a halogen atom, a hydroxy group, etc.

$A^1$ may be, for example, a substituted or unsubstituted aromatic group, such as a benzene group, a naphthalene group, a biphenyl group, a pyrene group, a perylene group, a benzoperylene group, a coronene group, or a combination thereof.

A¹ may be a polycyclic aromatic group, and may be, for example, a pyrene group, a perylene group, a benzoperylene group, a coronene group, or a combination thereof.

A¹ may be a substituted cyclic group and may be substituted with, for example, a hydroxy group, a thionyl group, a thiol group, a cyano group, a substituted or unsubstituted amino group, a substituted or unsubstituted C1 to C30 alkyl group, a substituted or unsubstituted C1 to C20 alkylamine group, or a substituted or unsubstituted C1 to C30 alkoxy group.

X¹ may be, for example, a hydroxy group.

According to an example embodiment, the monomer may be represented by, for example, the following Chemical Formula 2, Chemical Formula 3, or Chemical Formula 4.

[Chemical Formula 2]

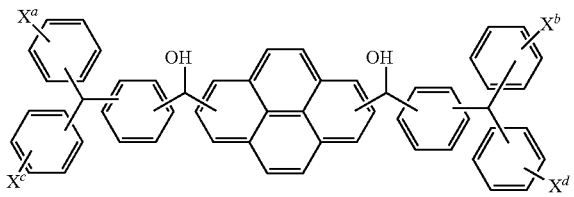

[Chemical Formula 3]

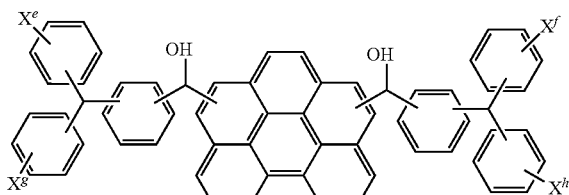

[Chemical Formula 4]

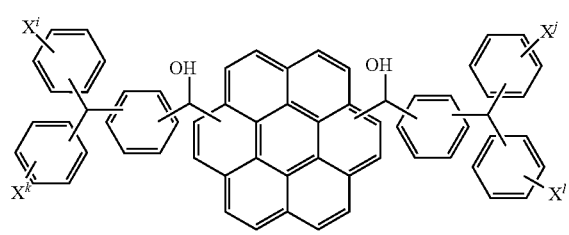

In the present example embodiment, in the above Chemical Formulas 2 to 4, $X^a$, $X^b$, $X^c$, $X^d$, $X^e$, $X^f$, $X^g$, $X^h$, $X^i$, $X^j$, $X^k$, and $X^l$ are independently a hydroxy group, a thionyl group, a thiol group, a cyano group, a substituted or unsubstituted amino group, a substituted or unsubstituted C1 to C30 alkyl group, a substituted or unsubstituted C1 to C20 alkylamine group, or a substituted or unsubstituted C1 to C30 alkoxy group.

The monomer may have a molecular weight of, for example, about 300 to about 3,000. When the monomer has a molecular weight within the above range, solubility of the monomer having a high carbon content for a solvent may be improved and an improved thin layer may be obtained through spin-on coating.

Hereinafter, a hardmask composition according to an example embodiment is described.

A hardmask composition according to an example embodiment includes the monomer and a solvent.

The monomer is the same as described above, and one kind of the monomer may be used singularly and two or more kinds of the monomers may be mixed.

The solvent may be a suitable having sufficient dissolubility or dispersion for the monomer and may be, for example, at least one selected from propylene glycol, propylene glycol diacetate, methoxy propanediol, diethylene glycol, diethylene glycol butylether, tri(ethyleneglycol)monomethylether, propylene glycol monomethylether, propylene glycol monomethylether acetate, cyclohexanone, ethyl lactate, gamma-butyrolactone, methylpyrrolidone, acetylacetone, and ethyl 3-ethoxypropionate.

The monomer may be included in an amount of, for example, about 1 to 50 wt % based on the total amount of the hardmask composition. When the monomer is included in the above range, a thickness of a coated thin film may be obtained.

The hardmask composition may further include a surfactant.

The surfactant may include, for example, an alkylbenzene sulfonate salt, an alkyl pyridinium salt, a polyethylene glycol, a quaternary ammonium salt, etc.

The surfactant may be included in an amount of, for example, about 0.001 to 3 parts by weight based on 100 parts by weight of the hardmask composition. Within the amount range, the solubility may be secured while helping to avoid changes in the optical properties of the hardmask composition.

Hereafter, a method for forming patterns according to an example embodiment using the hardmask composition is described.

A method of forming patterns according to an example embodiment includes providing a material layer on a substrate, applying the hardmask composition including the monomer and solvent on the material layer, heat-treating the hardmask composition to form a hardmask layer, forming a silicon-containing thin layer on the hardmask layer, forming a photoresist layer on the silicon-containing thin layer, exposing and developing the photoresist layer to form a photoresist pattern, selectively removing the silicon-containing thin layer and the hardmask layer using the photoresist pattern to expose a part of the material layer and etching an exposed part of the material layer.

The substrate may be, for example, a silicon wafer, a glass substrate, or a polymer substrate.

The material layer is a material to be finally patterned, for example, a metal layer such as an aluminum layer or a copper layer, a semiconductor layer such as a silicon layer, or an insulation layer such as a silicon oxide layer or a silicon nitride layer. The material layer may be formed through a method such as a chemical vapor deposition (CVD) process.

The hardmask composition may be applied by spin-on coating in a form of a solution. Herein, the hardmask composition may be applied at a thickness, for example, about 50 Å to about 50,000 Å.

The heat-treating the hardmask composition may be performed, for example, at about 100 to 500° C. for about 10 seconds to 10 minutes. During heat-treating, the monomer may cause a self cross-linking and/or mutual cross-linking reaction.

The silicon-containing thin layer may be made of, for example, silicon nitride or silicon oxide.

A bottom antireflective coating (BARC) may be further formed on the silicon-containing thin layer.

Exposure of the photoresist layer may be performed using, for example, ArF, KrF, or EUV. After exposure, heat treatment may be performed at, for example, about 100° C. to about 500° C.

The etching process of the exposed part of the material layer may be performed through a dry etching process using an etching gas and the etching gas may be, for example, $CHF_3$, $CF_4$, $Cl_2$, $BCl_3$, a mixed gas thereof, etc.

The etched material layer may be formed in a plurality of patterns, and the plurality of patterns may be, for example, a metal pattern, a semiconductor pattern, an insulation pattern, etc., which may be, for example, diverse patterns of a semiconductor integrated circuit device.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Synthesis of Monomer

Synthesis Example 1

First Step: Friedel-Crafts Acylation Reaction 50.0 g (0.23 mol) of pyrene, 194.4 g (0.53 mol) of 4-bis-4-methoxyphenyl-methylbenzoylchloride, and 818 g of 1,2-dichloroethane were mixed to prepare a solution in a flask. Subsequently, 70.6 g (0.53 mol) of aluminum chloride was slowly added to the solution at room temperature, and the mixture was heated up to 60° C. and then, agitated for 8 hours. When the reaction was complete, a precipitate obtained by adding methanol to the resultant was filtered and dried.

Second Step: Demethylation Reaction 50.0 g (0.06 mol) of the compound synthesized in the first step, 12.1 g (0.06 mol) of 1-dodecanethiol, 3.9 g (0.07 mol) of potassium hydroxide, and 165 g of N,N-dimethyl formamide were put in a flask and agitated at 120° C. for 8 hours. Subsequently, the mixture was cooled down and neutralized into about pH 7 by using a 10% hydrogen chloride solution and then, extracted by using ethyl acetate and dried.

Third Step: Reduction Reaction 30.0 g (0.04 mol) of the compound obtained in the second step and 230 g of tetrahydrofuran were put in a flask, preparing a solution. Subsequently, 15.1 g (0.4 mol) of a sodium borohydride aqueous solution was slowly added to the solution, and the mixture was agitated at room temperature for 24 hours. When the reaction was complete, the resultant was neutralized into about pH 7 by using a 10% hydrogen chloride solution and then, extracted with ethyl acetate and dried, obtaining a compound represented by the following Chemical Formula 2a.

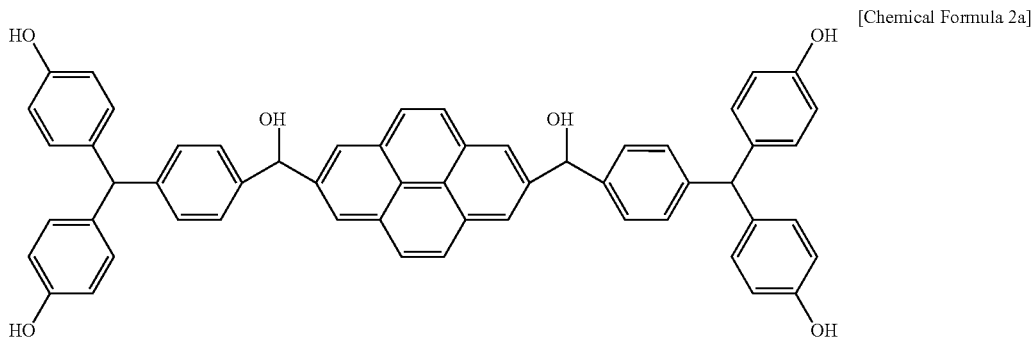

[Chemical Formula 2a]

Synthesis Example 2

First Step: Friedel-Crafts Acylation Reaction

A compound was synthesized according to the same method as Synthesis Example 1 except for using 50.0 g (0.18 mol) of benzoperylene, 150.4 g (0.41 mol) of 4-bis-4-methoxyphenyl-methylbenzoylchloride, 54.6 g (0.41 mol) of aluminum chloride, and 850 g of 1,2-dichloroethane.

Second Step: Demethylation Reaction

A compound was synthesized according to the same method as Synthesis Example 1 except for using 50.0 g (0.05 mol) of the compound synthesized in the first step, 10.08 g (0.05 mol) of 1-dodecanethiol, 3.4 g (0.06 mol) of potassium hydroxide, and 158 g of N,N-dimethyl formamide.

Third Step: Reduction Reaction

A compound represented by the following Chemical Formula 3a was obtained according to the same method as Synthesis Example 1 except for using 30.0 g (0.03 mol) of the compound synthesized in the second step, 11.3 g (0.3 mol) of a sodium borohydride aqueous solution, and 230 g of tetrahydrofuran.

[Chemical Formula 3a]

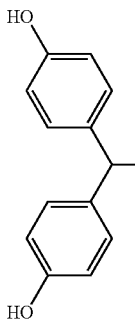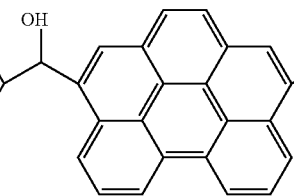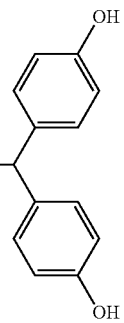

Synthesis Example 3

First Step: Friedel-Crafts Acylation Reaction

A compound was prepared according to the same method as Synthesis Example 1 except for using 50.0 g (0.17 mol) of coronene, 143.1 g (0.39 mol) of 4-bis-4-methoxyphenyl-methylbenzoylchloride, 51.9 g (0.39 mol) of aluminum chloride, and 816 g of 1,2-dichloroethane.

Second Step: Demethylation Reaction

A compound was prepared according to the same method as Synthesis Example 1 except for using 50.0 g (0.05 mol) of the compound synthesized in the first step, 10.08 g (0.05 mol) of 1-dodecanethiol, 3.4 g (0.06 mol) of potassium hydroxide, and 158 g of N,N-dimethyl formamide.

Third Step: Reduction Reaction

A compound represented by the following Chemical Formula 4a was prepared according to the same method as Synthesis Example 1 except for using 30.0 g (0.03 mol) of the compound synthesized in the second step, 11.3 g (0.3 mol) of a sodium borohydride aqueous solution, and 230 g of tetrahydrofuran.

[Chemical Formula 4a]

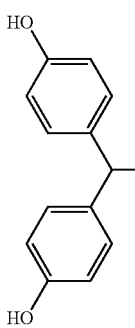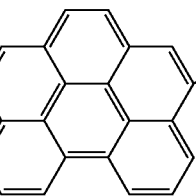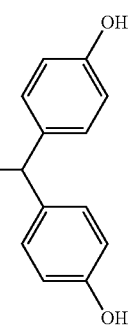

Comparative Synthesis Example 1

First Step: Friedel-Crafts Acylation Reaction

A solution was prepared by putting 10.0 g (0.0495 mol) of pyrene, 13.9 g (0.0989 mol) of benzoyl chloride, and 87 g of 1,2-dichloroethane in a flask. Subsequently, 13.2 g (0.0989 mol) of aluminum chloride was slowly added to the solution at room temperature and then, heated up to 60° C. and agitated for 8 hours. When the reaction was complete, a precipitate was obtained by adding methanol to the resultant and filtered, obtaining dibenzoylpyrene.

Second Step: Reduction Reaction 5.00 g (0.0122 mol) of dibenzoylpyrene and 57 g of tetrahydrofuran were put in a flask to prepare a solution. Subsequently, 4.60 g (0.122 mol) of a sodium borohydride aqueous solution was slowly added to the solution, and the mixture was agitated at room temperature for 24 hours. When the reaction was complete, the resultant was neutralized into about pH 7 by using a 5% hydrogen chloride solution and extracted with ethyl acetate and then, dried, obtaining a compound represented by the following Chemical Formula 5.

[Chemical Formula 5]

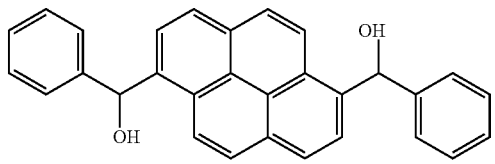

Preparation of Hardmask Composition

Example 1

A hardmask composition was prepared by dissolving the compound synthesized in Synthesis Example 1 in a mixed solvent of propyleneglycol monomethyl ether acetate (PGMEA) and cyclohexanone in a volume ratio of 7:3 (v/v) followed by filtering the resultant.

Example 2

A hardmask composition was prepared according to the same method as Example 1 except for using the compound according to Synthesis Example 2 instead of the compound according to Synthesis Example 1.

Example 3

A hardmask composition was prepared according to the same method as Example 1 except for using the compound according to Synthesis Example 3 instead of the compound according to Synthesis Example 1.

Comparative Example 1

A hardmask composition was prepared according to the same method as Example 1 except for using the compound according to Comparative Synthesis Example 1 instead of the compound according to Synthesis Example 1.

Evaluation 1: Chemical Resistance

Each hardmask layer was formed by respectively spin-coating the hardmask compositions according to Examples 1 to 3 and Comparative Example 1 on a silicon wafer and heat-treating the coated silicon wafers at 240° C. for 1 minute. Initial thicknesses of the hardmask layers were measured.

Subsequently, the hardmask layers were dipped in a KrF thinner peeling solution for 1 minute, and then thicknesses of the hardmask layers were measured again.

Thickness changes of the hardmask layers were measured by using a thin film thickness-measuring device made by K-MAC, and thickness decrease rates were calculated according to the following Calculation Equation 1.

(thin film thickness before dipping−thin film thickness after dipping)/thin film thickness before dipping× 100(%)     [Calculation Equation 1]

The results are provided in the following Table 1.

TABLE 1

| | Thickness decrease rate (%) |
|---|---|
| Example 1 | Less than or equal to 1% |
| Example 2 | Less than or equal to 1% |
| Example 3 | Less than or equal to 1% |
| Comparative Example 1 | Greater than or equal to 10% |

Referring to Table 1, the hardmask layers formed of the hardmask compositions according to Examples 1 to 3 showed a smaller thickness decrease rate after being dipped in a peeling solution than the hardmask layers formed of the hardmask compositions according to Comparative Example 1.

Accordingly, the hardmask compositions according to Examples 1 to 3 were sufficiently cross-linked compared with the hardmask composition according to Comparative Example 1 despite the heat treatment a relatively low temperature of 240° C. and formed a thin film having high chemical resistance.

Evaluation 2: Heat Resistance

The hardmask compositions according to Examples 1 to 3 and Comparative Example 1 were spin-on coated on a silicon wafer and heat-treated at 240° C. for 1 minute, each forming a hardmask layer. Subsequently, thicknesses of the thin films were measured. Subsequently, the thin films were additionally heat-treated at 400° C. for 2 minutes, and their thicknesses were measured again. The thicknesses of the thin films were used to calculate a thickness decrease rate was calculated based on according to the following Calculation Equation 2.

(thin film thickness after heat treatment at 240° C.−thin film thickness after heat treatment at 400° C.)/thin film thickness after heat treatment at 240° C.×100(%)     [Calculation Equation 2]

The results are provided in Table 2.

TABLE 2

| | Thickness decrease rate of thin film (%) |
|---|---|
| Example 1 | Less than or equal to 10% |
| Example 2 | Less than or equal to 10% |
| Example 3 | Less than or equal to 10% |
| Comparative Example 1 | Greater than or equal to 20% |

Referring to Table 2, the hardmask layers formed of the hardmask compositions according to Examples 1 to 3 showed a smaller thickness decrease rate at a high temperature than that of the hardmask layers formed of the hardmask compositions according to Comparative Example 1.

Accordingly, the hardmask compositions according to Examples 1 to 3 turned out to have higher heat resistance than the hardmask composition according to Comparative Example 1.

Evaluation 3: Pattern Formation

Each hardmask layer was formed by spin-on coating the hardmask compositions according to Examples 1 to 3 and Comparative Example 1 on a silicon wafer and heat-treating the coated silicon wafers at 240° C. for 60 seconds. Subsequently, the hardmask layers were coated with a photoresist for KrF, and then baked at 110° C. for 60 seconds, exposed by using an exposure equipment made by ASML (XT:1400, NA 0.93), and developed by using tetramethyl ammonium hydroxide (a 2.38 wt % aqueous solution). Subsequently, the patterned specimens were respectively dry-etched by using a $CHF_3/CF_4$ mixed gas and then a $BCl_3/Cl_2$ mixed gas. Organic materials remaining in the specimens were removed by using an oxygen gas, and the cross-section of the specimens were examined by using a FE SEM.

The results are provided in Table 3.

TABLE 3

|  | Pattern profile |
|---|---|
| Example 1 | Vertical |
| Example 2 | Vertical |
| Example 3 | Vertical |
| Comparative Example 1 | Tapered |

Referring to Table 3, the hardmask layers formed of the hardmask compositions according to Examples 1 to 3 were all vertically patterned, while the hardmask layer formed of the hardmask composition according to Comparative Example 1 was patterned in a tapered shape.

Accordingly, the hardmask compositions according to Examples 1 to 3 had excellent etching resistance and formed an excellent pattern compared with the hardmask composition according to Comparative Example 1.

By way of summation and review, a typical lithographic technique includes providing a material layer on a semiconductor substrate, coating a photoresist layer thereon, exposing and developing the same to provide a photoresist pattern, and etching the material layer using the photoresist pattern as a mask. According to small-sizing the pattern to be formed, it may be difficult to provide a fine pattern having an excellent profile by the typical lithographic technique. Accordingly, a layer, called a hardmask layer, may be formed between the material layer and the photoresist layer to provide a fine pattern.

The hardmask layer plays a role of an intermediate layer for transferring the fine pattern of photoresist to the material layer through the selective etching process. Accordingly, the hardmask layer is desired to have characteristics such as heat resistance, etch resistance, and the like to tolerate multiple etching processes.

A hardmask layer may be formed by a spin-on coating method instead of chemical vapor deposition. The spin-on coating method uses a hardmask composition having dissolubility for a solvent. A monomer compound, of which solubility may be easily controlled in a hardmask composition, may be used. However, it is desired that the monomer compound provide chemical resistance and heat resistance compared with a polymer in a hardmask composition.

As described above, embodiments provide a monomer for a hardmask composition, which may provide improved gap-fill characteristics and planarization characteristics during spin-on coating, along with chemical resistance, heat resistance, and etching resistance. Another embodiment provides a hardmask composition including the monomer. Yet another embodiment provides a method of forming patterns using the hardmask composition. The monomer for a hardmask composition may be applied to a spin-on coating method, and may provide chemical resistance, heat resistance, and etch resistance.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A monomer for a hardmask composition, the monomer being represented by the following Chemical Formula 1:

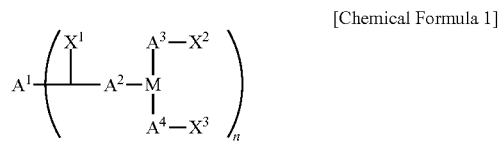

[Chemical Formula 1]

wherein, in the above Chemical Formula 1, $A^1$ is a substituted or unsubstituted aliphatic cyclic group or a substituted or unsubstituted aromatic cyclic group, $A^2$ to $A^4$ are each a phenylene group, $X^1$ is a hydroxy group, a thionyl group, a thiol group, a cyano group, a substituted or unsubstituted amino group, a substituted or unsubstituted C1 to C20 alkylamine group, or a substituted or unsubstituted C1 to C30 alkoxy group, $X^2$ and $X^3$ are each independently a hydroxy group, a thionyl group, a thiol group, a cyano group, a substituted or unsubstituted amino group, a substituted or unsubstituted C1 to C30 alkyl group, a substituted or unsubstituted C1 to C20 alkylamine group, or a substituted or unsubstituted C1 to C30 alkoxy group, M is $CR^a$, $SiR^b$, N, P, $PR^cR^d$, or $PR^e$, wherein $R^a$, $R^b$, $R^c$, and $R^d$ are each independently hydrogen, a substituted or unsubstituted C1 to C10 alkyl group, a halogen atom, a halogen-containing group, or a combination thereof, and $R^e$ is oxygen (O) or sulfur (S), and n is an integer ranging from 1 to 4.

2. The monomer as claimed in claim 1, wherein $A^1$ is a substituted or unsubstituted cyclic group selected from the following Group 1:

[Group 1]

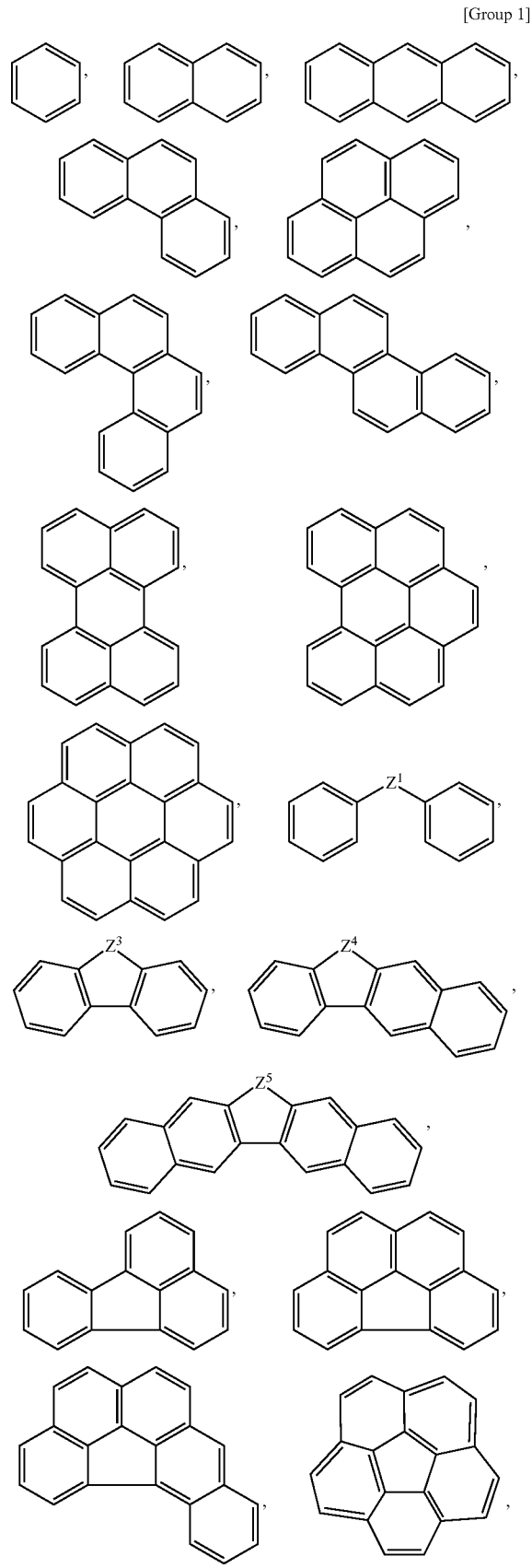

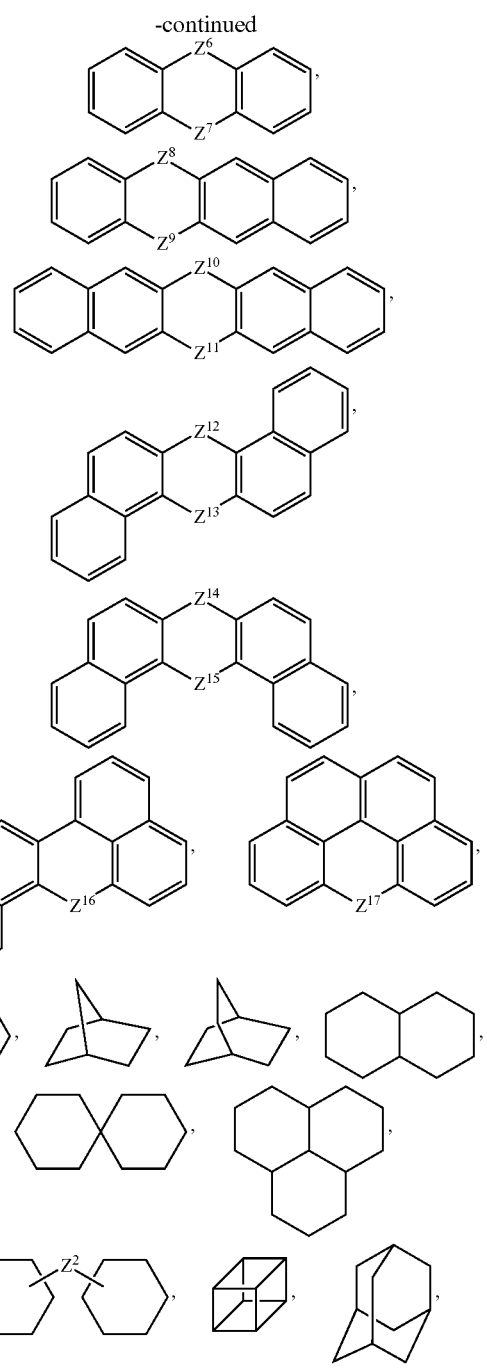

wherein, in Group 1, $Z^1$ and $Z^2$ are each independently a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, C=O, $NR^f$, oxygen (O), sulfur (S), or a combination thereof, wherein $R^f$ is hydrogen, a substituted or unsubstituted C1 to C10 alkyl group, a halogen atom, or a combination thereof, and $Z^3$ to $Z^{17}$ are independently C=O, $NR^g$, oxygen (O), sulfur (S), $CR^hR^i$, or a combination thereof, wherein $R^g$ to $R^i$ are each independently hydrogen, a substituted or unsubstituted C1 to C10 alkyl group, a halogen atom, a halogen-containing group, or a combination thereof.

3. The monomer as claimed in claim 1, wherein $X^1$ is a hydroxy group.

4. The monomer as claimed in claim 1, wherein:
$A^1$ is a substituted or unsubstituted divalent pyrene, benzoperylene, or coronene group,
$A^2$ to $A^4$ are each a phenylene group,
$X^1$ is a hydroxy group, and $X^2$ to $X^3$ are each independently a hydroxy group, a thionyl group, a thiol group, a cyano group, a substituted or unsubstituted amino group, a substituted or unsubstituted C1 to C30 alkyl group, a substituted or unsubstituted C1 to C20 alkylamine group, or a substituted or unsubstituted C1 to C30 alkoxy group,
M is $CR^a$, wherein $R^a$ is hydrogen, a substituted or unsubstituted C1 to C10 alkyl group, a halogen atom, a halogen-containing group, or a combination thereof, and
n is 2.

5. The monomer as claimed in claim 1, wherein the monomer is represented by the following Chemical Formula 2, Chemical Formula 3, or Chemical Formula 4:

[Chemical Formula 2]

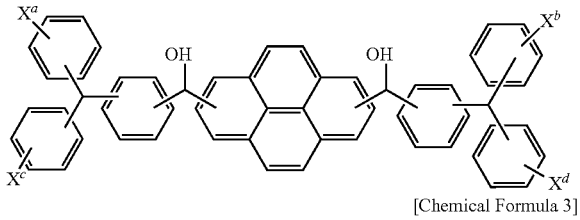

[Chemical Formula 3]

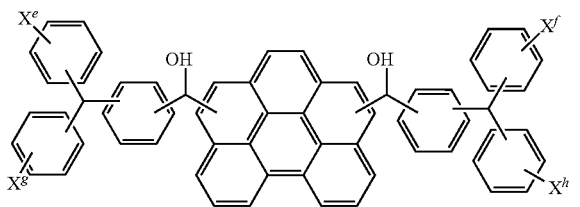

[Chemical Formula 4]

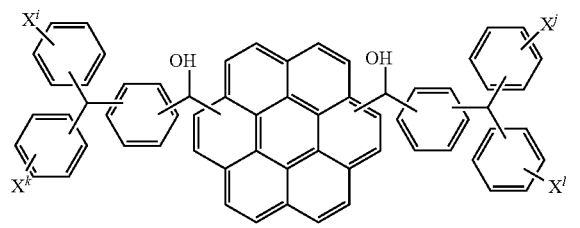

wherein, in the above Chemical Formulae 2 to 4,
$X^a$, $X^b$, $X^c$, $X^d$, $X^e$, $X^g$, $X^h$, $X^i$, $X^j$, $X^k$, and $X^l$ are each independently a hydroxy group, a thionyl group, a thiol group, a cyano group, a substituted or unsubstituted amino group, a substituted or unsubstituted C1 to C30 alkyl group, a substituted or unsubstituted C1 to C20 alkylamine group, or a substituted or unsubstituted C1 to C30 alkoxy group.

6. The monomer as claimed in claim 1, wherein the monomer has a molecular weight of about 300 to about 3,000.

7. A hardmask composition, comprising:
a monomer represented by the following Chemical Formula 1; and
a solvent,

[Chemical Formula 1]

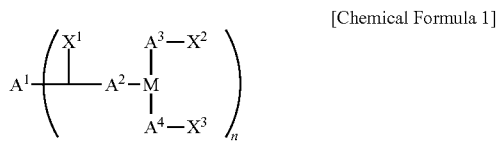

wherein, in the above Chemical Formula 1,
$A^1$ is a substituted or unsubstituted aliphatic cyclic group or a substituted or unsubstituted aromatic cyclic group,
$A^2$ to $A^4$ are each a phenylene group,
$X^1$ is a hydroxy group, a thionyl group, a thiol group, a cyano group, a substituted or unsubstituted amino group, a substituted or unsubstituted C1 to C20 alkylamine group, or a substituted or unsubstituted C1 to C30 alkoxy group,
$X^2$ and $X^3$ are each independently a hydroxy group, a thionyl group, a thiol group, a cyano group, a substituted or unsubstituted amino group, a substituted or unsubstituted C1 to C30 alkyl group, a substituted or unsubstituted C1 to C20 alkylamine group, or a substituted or unsubstituted C1 to C30 alkoxy group,
M is $CR^a$, $SiR^b$, N, P, $PR^cR^d$, or $PR^e$, wherein $R^a$, $R^b$, $R^c$, and $R^d$ are each independently hydrogen, a substituted or unsubstituted C1 to C10 alkyl group, a halogen atom, a halogen-containing group, or a combination thereof, and $R^e$ is oxygen (O) or sulfur (S), and
n is an integer ranging from 1 to 4.
$R^e$ is oxygen (O) or sulfur (S).

8. The hardmask composition as claimed in claim 7, wherein $A^1$ a substituted or unsubstituted cyclic group selected from the following Group 1:

[Group 1]

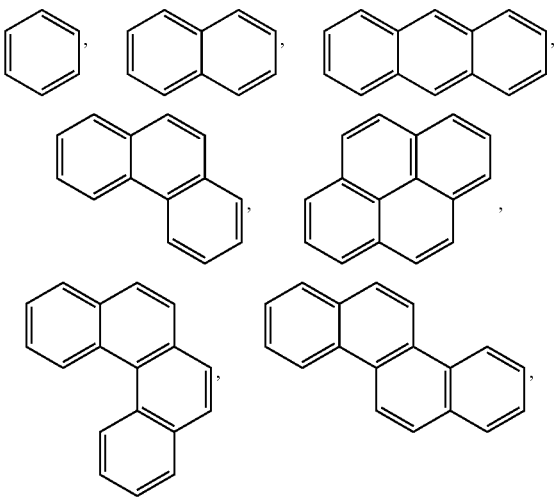

-continued

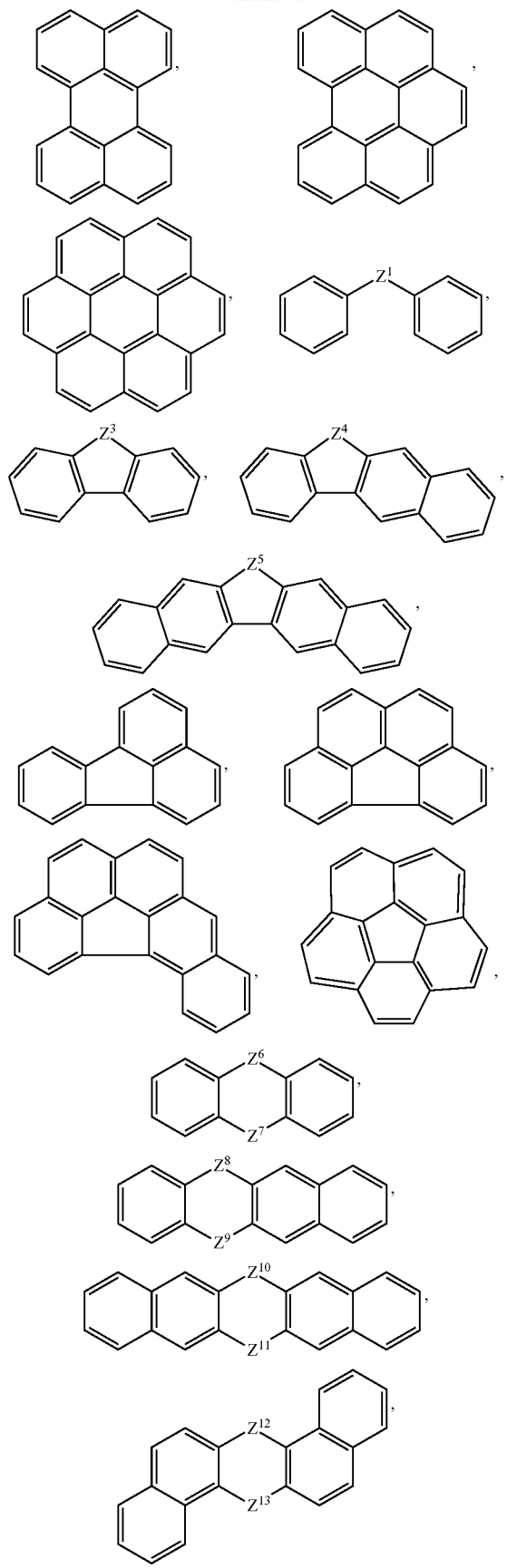

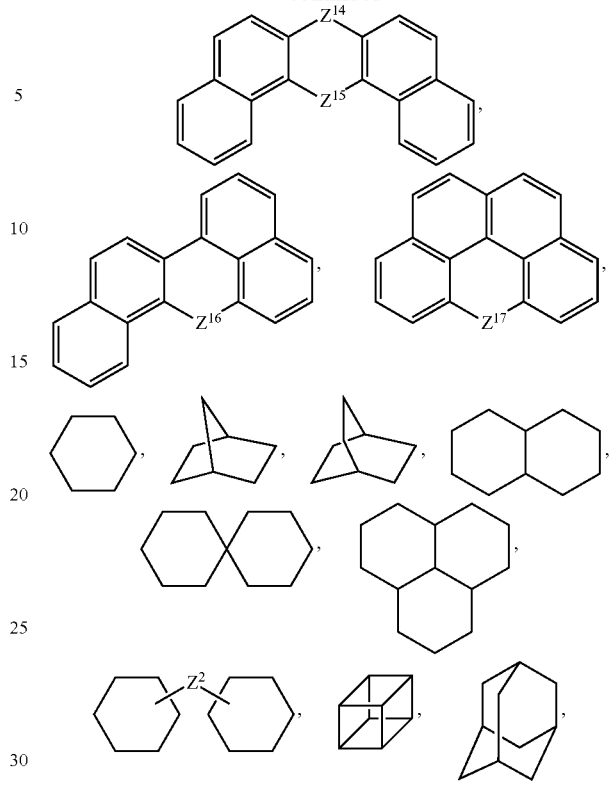

wherein, in Group 1, $Z^1$ and $Z^2$ are each independently a single bond, a substituted or unsubstituted C1 to C20 alkylene group, a substituted or unsubstituted C3 to C20 cycloalkylene group, a substituted or unsubstituted C6 to C20 arylene group, a substituted or unsubstituted C2 to C20 heteroarylene group, a substituted or unsubstituted C2 to C20 alkenylene group, a substituted or unsubstituted C2 to C20 alkynylene group, C=O, $NR^f$, oxygen (O), sulfur (S), or a combination thereof, wherein $R^f$ is hydrogen, a substituted or unsubstituted C1 to C10 alkyl group, a halogen atom, or a combination thereof, and $Z^3$ to $Z^{17}$ are independently C=O, $NR^g$, oxygen (O), sulfur (S), $CR^hR^i$, or a combination thereof, wherein $R^g$ to $R^i$ are each independently hydrogen, a substituted or unsubstituted C1 to C10 alkyl group, a halogen atom, a halogen-containing group, or a combination thereof.

9. The hardmask composition as claimed in claim 7, wherein the $X^1$ is a hydroxy group.

10. The hardmask composition as claimed in claim 7, wherein:

$A^1$ is a substituted or unsubstituted divalent pyrene, benzoperylene, or coronene group, $A^2$ to $A^4$ are each a phenylene group, $X^1$ is a hydroxy group, and $X^2$ to $X^3$ are each independently a hydroxy group, a thionyl group, a thiol group, a cyano group, a substituted or unsubstituted amino group, a substituted or unsubstituted C1 to C30 alkyl group, a substituted or unsubstituted C1 to C20 alkylamine group, or a substituted or unsubstituted C1 to C30 alkoxy group, M is $CR^a$, wherein $R^a$ is hydrogen, a substituted or unsubstituted C1 to C10 alkyl group, a halogen atom, a halogen-containing group, or a combination thereof, and n is 2.

11. The hardmask composition as claimed in claim 7, wherein the monomer is represented by the following Chemical Formula 2, Chemical Formula 3, or Chemical Formula 4:

[Chemical Formula 2]

[Chemical Formula 3]

[Chemical Formula 4]

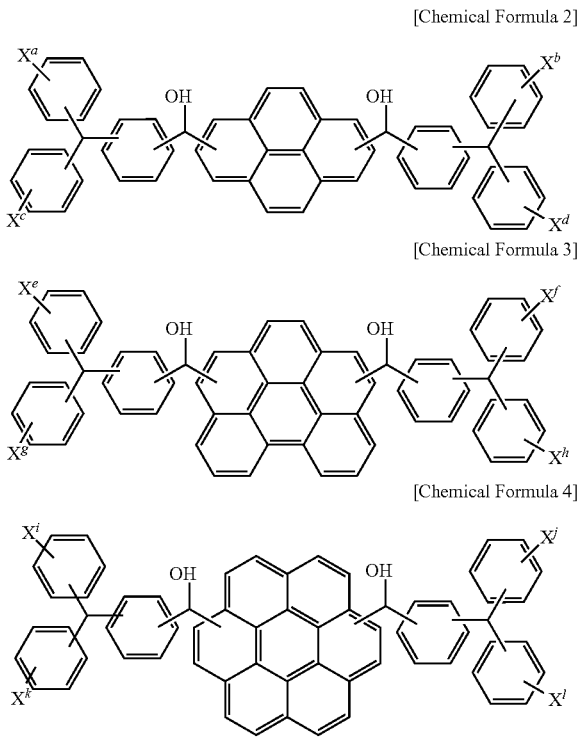

wherein, in the above Chemical Formulae 2 to 4,
$X^a$, $X^b$, $X^c$, $X^d$, $X^e$, $X^f$, $X^g$, $X^h$, $X^i$, $X^j$, $X^k$, and $X^l$ are each independently a hydroxy group, a thionyl group, a thiol group, a cyano group, a substituted or unsubstituted amino group, a substituted or unsubstituted C1 to C30 alkyl group, a substituted or unsubstituted C1 to C20 alkylamine group, or a substituted or unsubstituted C1 to C30 alkoxy group.

12. The hardmask composition as claimed in claim 7, wherein the monomer has a molecular weight of about 300 to about 3,000.

13. The hardmask composition as claimed in claim 7, wherein the monomer is included in an amount of about 1 to about 50 wt % based on the total amount of the hardmask composition.

14. A method of forming patterns, comprising:
providing a material layer on a substrate;
applying the hardmask composition as claimed in claim 7 on the material layer;
heat-treating the hardmask composition to form a hardmask layer;
forming a silicon-containing thin layer on the hardmask layer;
forming a photoresist layer on the silicon-containing thin layer;
exposing and developing the photoresist layer to form a photoresist pattern;
selectively removing the silicon-containing thin layer and the hardmask layer using the photoresist pattern to expose a part of the material layer; and
etching an exposed part of the material layer.

15. The method as claimed in claim 14, wherein the hardmask composition is applied using a spin-on coating method.

* * * * *